United States Patent [19] [11] Patent Number: 4,867,571
Frick et al. [45] Date of Patent: Sep. 19, 1989

[54] WAVE FORM FILTER PULSE DETECTOR AND METHOD FOR MODULATED SIGNAL

[75] Inventors: Gene Frick, Anaheim; Rex McCarthy, Whittier; Michael Pawlowski, Chino, all of Calif.

[73] Assignee: Sensormedics Corporation, Anaheim, Calif.

[21] Appl. No.: 317,097

[22] Filed: Feb. 28, 1989

Related U.S. Application Data

[63] Continuation of Ser. No. 911,956, Sep. 26, 1986, abandoned.

[51] Int. Cl.⁴ ...................... G01N 21/00; G01N 33/49
[52] U.S. Cl. ...................................... 356/436; 356/41; 128/633
[58] Field of Search ........................ 356/41, 432, 436; 364/550, 551, 572; 328/24, 117; 307/311, 358; 128/633

[56] References Cited

U.S. PATENT DOCUMENTS

| 2,706,927 | 4/1955 | Wood | 128/633 |
|---|---|---|---|
| 3,522,139 | 8/1970 | Coor et al. | 428/592 |
| 3,638,640 | 2/1972 | Shaw | 128/2 |
| 3,647,299 | 3/1972 | Lavallee | 356/41 |
| 3,799,672 | 3/1974 | Vurek | 356/41 |
| 3,842,355 | 10/1974 | Fleagle | 328/117 |
| 3,938,052 | 2/1976 | Glasson et al. | 328/117 |
| 3,992,672 | 11/1976 | Fasching | 328/117 |
| 3,998,550 | 12/1976 | Konishi et al. | 356/39 |
| 4,063,551 | 12/1977 | Sweeny | 128/2.05 P |
| 4,086,915 | 5/1978 | Kofsky et al. | 128/2 L |
| 4,093,988 | 6/1978 | Scott | 364/572 |
| 4,167,331 | 7/1980 | Nielson | 356/39 |
| 4,214,213 | 7/1980 | Ferrie | 307/358 |
| 4,260,951 | 4/1981 | Lewyn | 307/311 |
| 4,266,554 | 5/1981 | Hamaguri | 128/633 |
| 4,402,290 | 10/1983 | Wilber | 128/633 |
| 4,523,279 | 6/1985 | Sperinde et al. | 364/416 |

FOREIGN PATENT DOCUMENTS 0102816 3/1984 European Pat. Off. .
128387 10/1975 Japan .

OTHER PUBLICATIONS

Grover, "Improved Extracorporeal Reflectance Oximeter", Conference Proceedings of the 26th Annual Conference on Engineering in Medicine and Biology, Sep. 30–Oct. 4, 1973, p. 275.
Kramer et al., "Influence of Oxygen Saturation, Erythocyte Concentration and Optical Depth Upon the Red and Near-Infrared Light Transmittance of Whole Blood", American Journal of Physiology, 165:229-246 (1951).
Schibili et al., "An Electronic Circuit for Red/Infrared Oximeters", IEEE Transactions on Bio-Medical Engineering, vol. BME-25, No. 1, Jan., 1978.
Tait et al., "A Theoretical Analysis of Some Errors in Oximetry", IEE Transactions on Bio-Medical Engineering, vol. BME-13, No. 4, Oct., 1966.
Wood and Garci, "Photoelectric Determination of Arterial Oxygen Saturation in Man", J. Lab. Clin. Med. 34, pp. 387-401 (1949).

Primary Examiner—Vincent P. McGraw
Assistant Examiner—William L. Oen
Attorney, Agent, or Firm—Lyon & Lyon

[57] ABSTRACT

A device and method for determining pulses in a modulated signal is disclosed. The modulated signal is processed and converted into a quantized analog type of digital data stream. The data stream is evaluated over time by considering preceeding and subsequent values in the data stream to generate a filtered wave form. By using extreme values in the filtered wave form pulse detection is accurately determined regardless of whether the modulated signal has complicating features, such as dicrotic notch, or high noise levels, or both.

17 Claims, 5 Drawing Sheets

OXIMETER HARDWARE BLOCK DIAGRAM

OXIMETER HARDWARE BLOCK DIAGRAM

WAVE FORM FILTER PULSE DETECTOR AND METHOD FOR MODULATED SIGNAL

This is a continuation of co-pending application Ser. No. 911,956 filed on Sept. 26, 1986, now abandoned.

BACKGROUND AND SUMMARY OF THE INVENTION

The present invention relates to a device and method for detecting the pulse in a modulated signal. Specifically, the invention relates to the accurate detection of a pulse even if the modulated signal has complicating features such as dicrotic notch, or high noise levels, or both.

A modulated signal is generated, for example, by transmitting light through living tissue and monitoring changes in intensity of the transmitted light. Circuit means are provided for signal processing and a microprocessor for mathematical evaluation of the changes in the transmitted light. The processing includes signal separation, noise reduction, amplification and an analog to digital conversion. The processed signal is mathematically evaluated over time by considering preceeding and subsequent values in the data stream to generate a filtered wave form. By using an extreme value in the filtered wave form pulse detection can be accurately determined.

BRIEF DESCRIPTION OF THE DRAWINGS

FIG. 5b is the filtered data stream of FIG. 5a.

DETAILED DESCRIPTION OF THE PREFERRED EMBODIMENT

Figure 1:
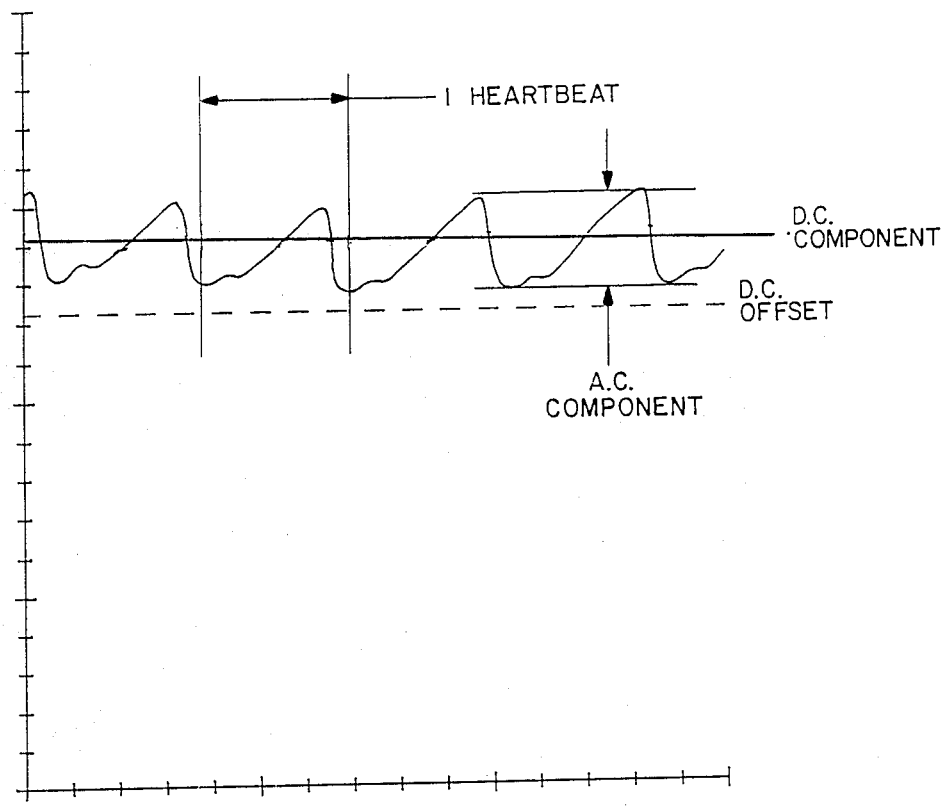
FIG. 1 is a data stream showing the A.C. component, the D.C. component, and the D.C. offset.

The invention can be best understood by first examining typical analog modulated signals, or values of the data points in the data stream following the analog to digital conversion. In each instance, FIGS. 1-5b, the y-axis represents the electrical signal, e.g., voltage, and the x-axis represents time. FIG. 1 depicts a relatively noise free data stream without a baseline drift. The data stream comprises a DC component and an AC component. The DC component further comprises a DC offset and DC remainder. The AC component to the DC component, is small. To simplify the evaluation of the AC signal, necessary for the pulse determination, the DC offset is removed. The remaining signal is thereafter amplified. The data stream of FIG. 1 after removal of the D.C. offset and amplification is shown in FIG. 2.

Figure 2:
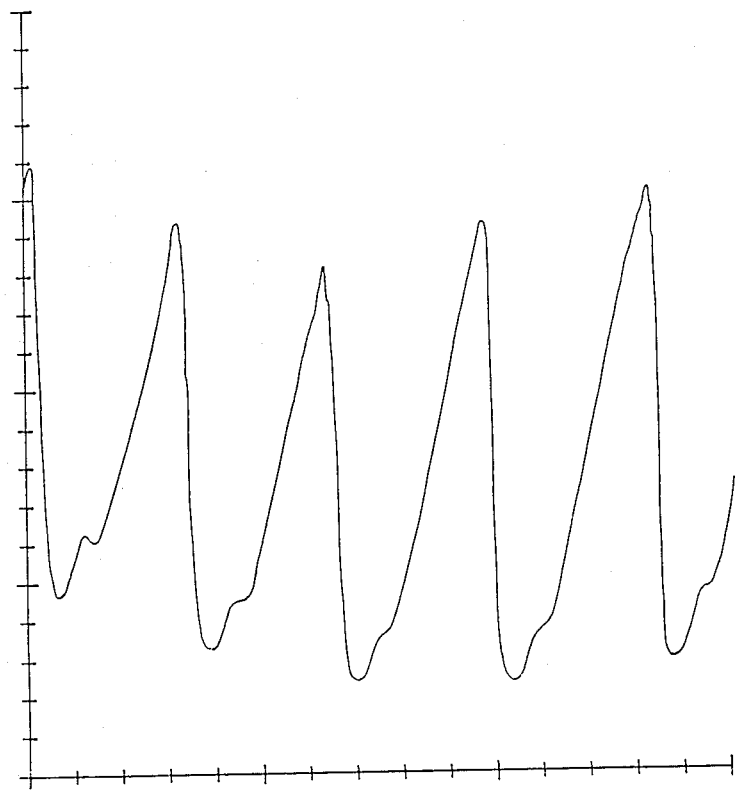
FIG. 2 is the data stream of FIG. 1 following removal of the D.C. offset and following amplification.
Figure 3:
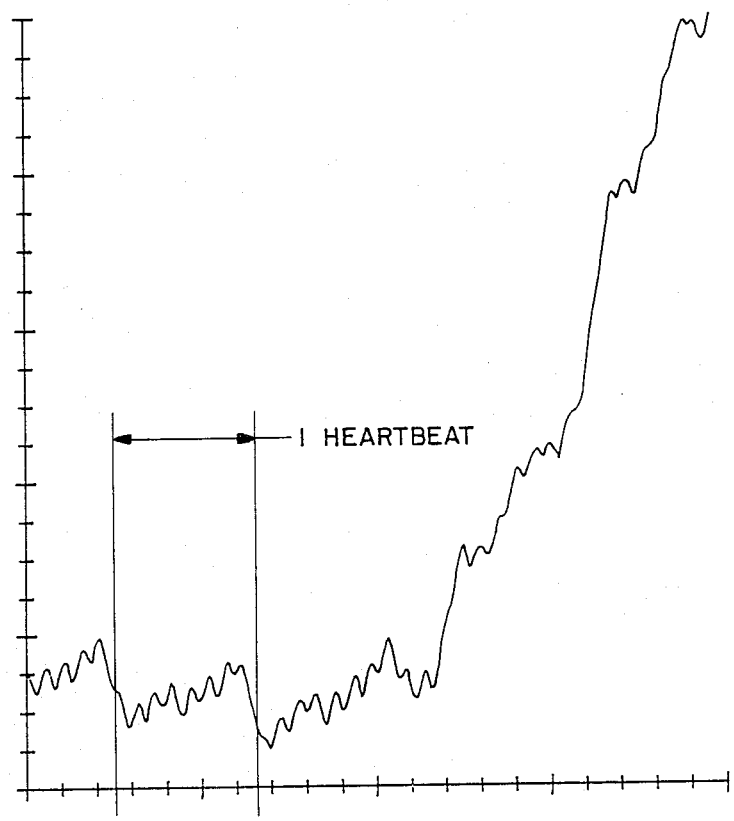
FIG. 3 is a noisy data stream with a complicating feature known as baseline drift.
Figure 4:
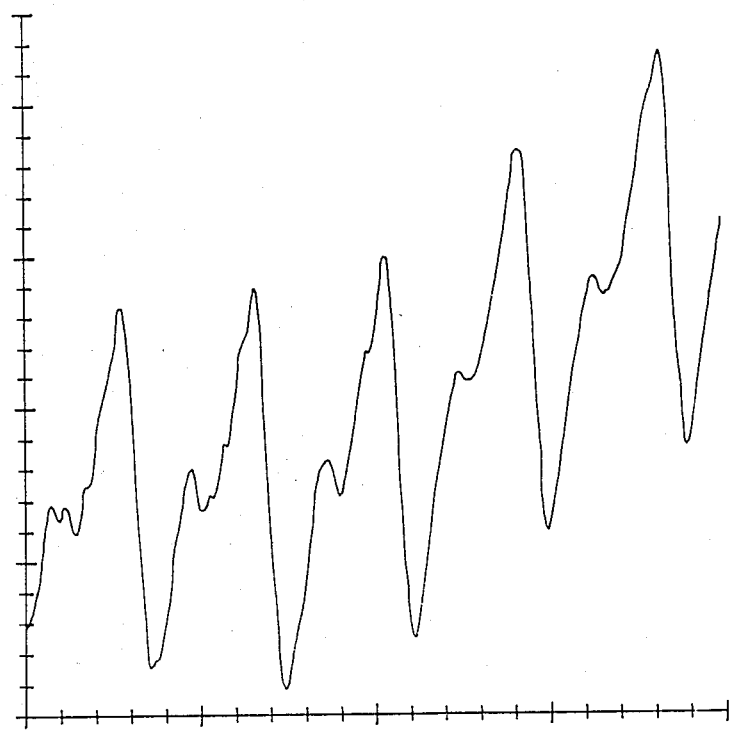
FIG. 4 is a data stream following removal of the D.C. offset and following amplification with a complicating feature known as a dicrotic notch.
Figure 5A:
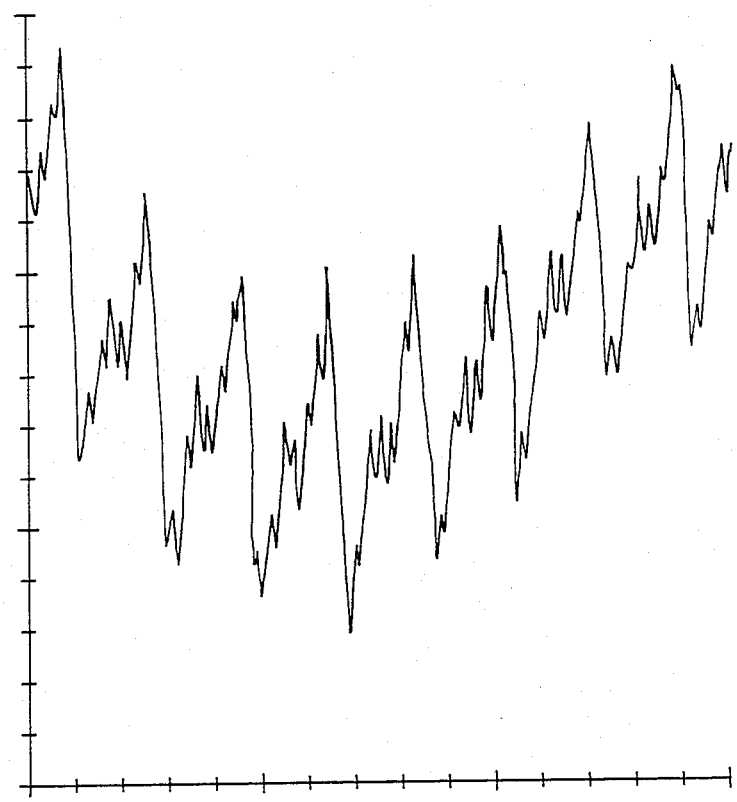
FIG. 5a is a data stream similar to FIG. 4, but with substantial noise.
Figure 5B:
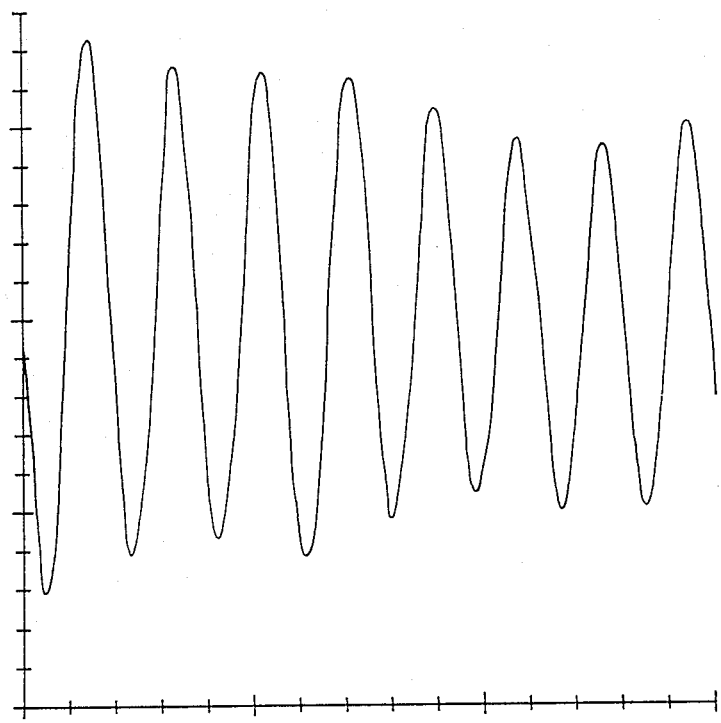

The signal of FIGS. 1 and 2 is a relatively clean data stream. However, many data streams are substantially more complicated. FIG. 3 depicts a complex data stream, that is both noisy and has a substantial baseline drift. Another data stream, shown in FIG. 4, following removal of the DC offset and following amplification has a complicating feature known as a dicrotic notch. The data stream of FIG. 5a is similar to that shown in FIG. 4. However, the FIG. 5a data stream has the additional complicating factor of a high noise level. FIG. 5b shows the data stream of FIG. 5a after filtering.

The operating principles of the pulse detector are described first. Associated with every given data point in the data stream and equidistant from that data point are multiple pairs of data points. That is, each data point has multiple pairs of associated data points. For each pair, the first associated data point occurs some time prior to the given data point and the second associated data point occurs an equal amount of time after the given data point. A difference is found by subtracting the detected values for the associated data points one from another. The difference for each pair of associated data points is then summed to form the output of a wave form filter for the given point. The total time spanned by these associated points is called the wave form filter length. This can be expressed in the following fashion:

$$F_i = \sum_{j=1}^{L} (P_{i+j} - P_{i-j})$$

Where $F_i$ is the wave form filter output for a given time $t_i$ having a data stream value $P_i$, $P_{i-j}$ is the data stream value at time $t_i - t_j$, $P_{i+j}$ is the data stream value at time $t_i + t_j$, and the wave form filter length is $2*L+1$. Using this approach to finding $F_i$ requires L subtractions and $L-1$ additions.

A simpler calculation of $F_{i+1}$ is possible if $F_i$ has already been computed. That is:

$$F_{i+1} = F_i + P_{i+L+1} + P_{i-L} - P_i - P_{i+1}$$

This calculation requires only two additions and two subtractions regardless of the length of the wave form filter. Present microprocessors are able to make this calculation in real time if the discrete points in the data stream occur at, for example, 15 millisecond intervals. For this calculation, memory of $2L+1$ values is required.

The accuracy of the output of the wave form filter for pulse detection is best when the wave form filter length and the pulse length of the signal are the same. When there is a large mismatch in these two quantities, the accuracy of the filter is diminished. Two methods have been found to overcome this problem. The first is to use two or more filters and examine each of them separately to determine which most closely matches the pulse length. The other is to combine two filters such that their combined output will work on any signal of interest. The second method requires four additions and four subtractions for each point.

Figure 6:
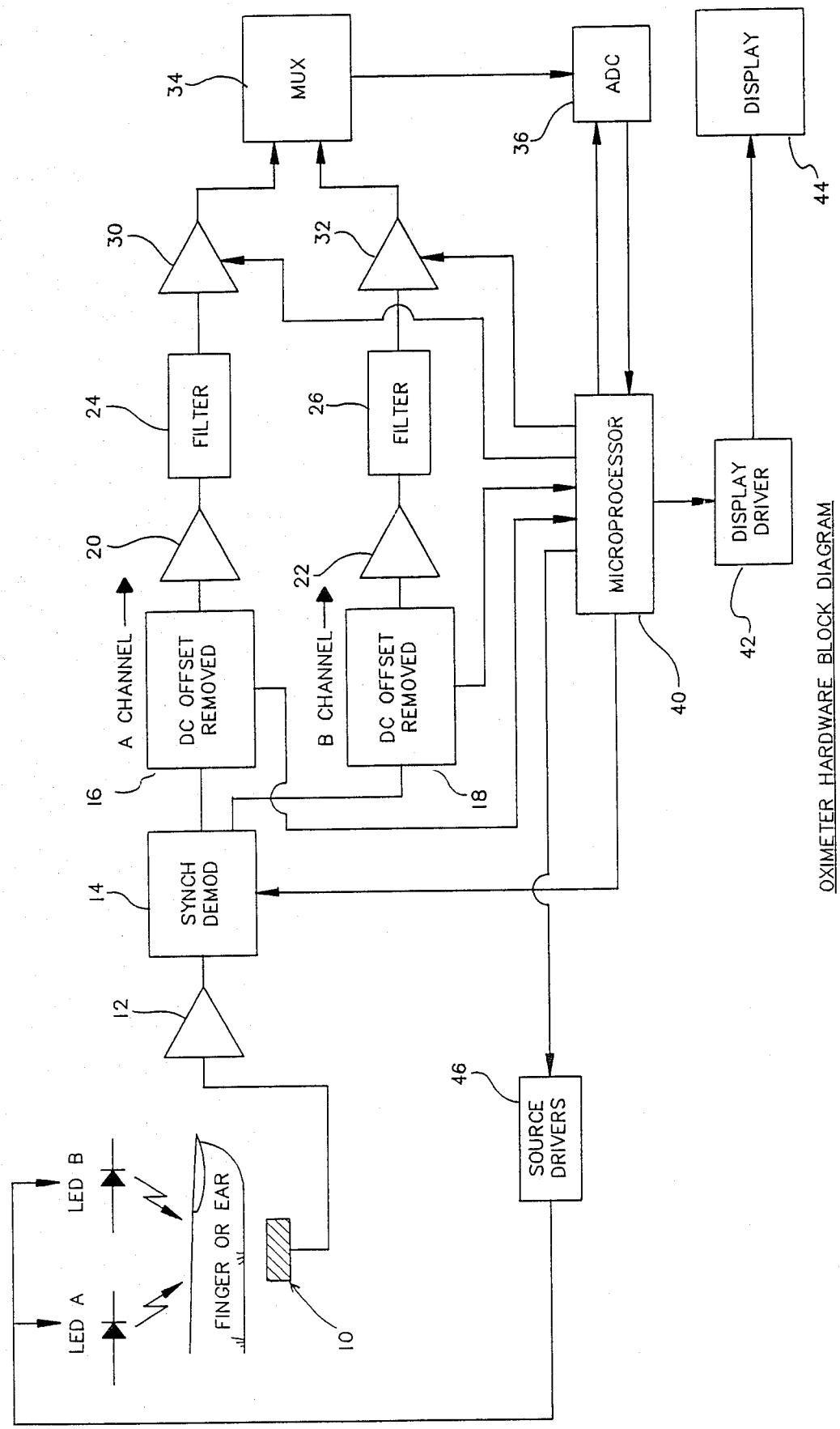
FIG. 6 is a block diagram of the hardware comprising an oximeter and pulse detector.

The modulated signal from which the pulse is determined may be one of the two signals used in determining oxygen saturation by means of an oximeter. The functioning of the pulse detector and, to some extent, an associated oximeter is now described. In FIG. 6, there is depicted a block diagram of the hardware used in an oximeter. A photoelectric transducer or photodiode 10 receives the light transmitted through a measuring point in the human body such as an ear lobe or finger. For the determination of oxygen saturation two light components are transmitted through the measuring point.

Light component A is transmitted from LED A and light component B is transmitted from LED B. If only the pulse is determined, only one light, either A or B, need be transmitted, processed and evaluated.

The data streams detected by photodiode 10 are amplified by pre-amplifer 12 and passed through the synchronized demodulator 14 to separate the data streams for each of the two light components. For each of the two data streams, the data stream is further separated (16 and 18) into a DC offset and the DC remainder plus the AC component. The values of the DC offset are sampled and held in the microprocessor 40 for further processing. Alternatively, the DC offset can be present at a fixed value. Once the DC offset is removed, data streams A and B are passed through operational amplifiers 20 and 22. The signal streams are amplified by fixed gains relative to the signal strengths of channel A and channel B. If the A channel processes the red signal, the fixed gain may be approximately a multiple of 200-250 of the preexisting data stream while, the B channel, if processing an infrared signal, the fixed gain may be approximately a multiple of 40-60 of the preexisting data stream.

The data streams of both channels A and B are passed through the filters 24 and 26 to reduce gross extraneous noise. The signal streams are then passed through variable attenuators 30 and 32, the control of which is performed by an evaluation of the signal strength made by the microprocessor 40. The signal streams are then inputted to multiplexor 34 where they are sampled and held until the analog to digital convertor 36 has converted each incoming analog signal into an outgoing digital also referred to as a quantized analogue signal signal.

Figure 7:
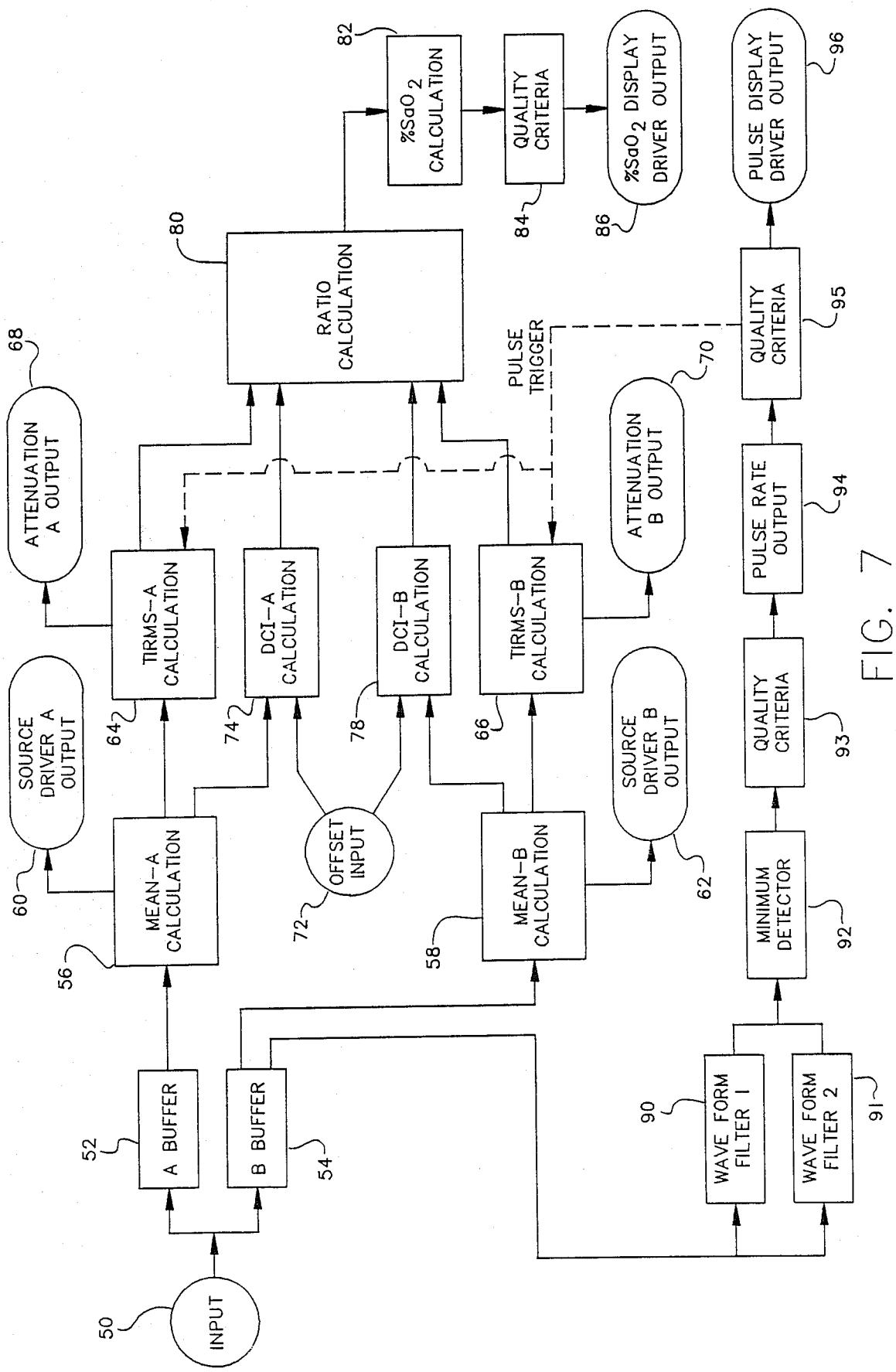
FIG. 7 is a process flow block diagram of the microprocessor unit of an oximeter and pulse detector.

The data streams are thereafter processed as shown in FIG. 7. As each data point in the data stream is inputted into the microprocessor 40, they are stored in buffers 52 and 54. As inputs are received the values are sequentially stored in the buffers replacing previous values which are shifted through and eventually out of the buffers. When the process is first started or after data is lost, the microprocessor 40 holds until the buffer is full before commencing a calculation.

Once the buffers fill, the wave form filter or filter outputs, if more than one wave form filter is used, are calculated (90, 91). The initial wave form filter output is determined by subtracting each successive trailing data point in the data streamm from each successive leading data point in the data stream and then summing these values. Each successive wave form filter output is determined by summing (i) the most recent wave form filter output, (ii) the trailing data point in the data stream, and (iii) the leading data point in the data stream for the most recent wave form filter output calculation and subtracting the sum of (i) the data point in the data stream halfway through the buffer and (ii) the data point in the data stream one data point beyond the halfway mark in the buffer. The foregoing mathematical calculation is performed for each wave form filter used.

Once the wave form filter outputs are determined, a detector 92 is used to determine an extreme value, such as a maximum or minimum. The rate of the extreme values are compared (93), by using quality criteria, with an expected range of values. If the extreme value is within the range of expected values, the pulse rate is determined (94). The pulse rate is also compared (95), by using quality criteria, with an expected range of pulse rates. If the pulse rate is within the range of expected values, the pulse rate is outputted to the pulse display driver (96).

While the above embodiments have been disclosed as the best mode presently contemplated by the inventor, it should be realized that these examples should not be interpreted as limiting, because an artisan skilled in this field, once given the present teachings, can vary from these specific embodiments. Accordingly, the scope of the present invention should be determined solely from the following claims.

We claim:

1. An apparatus for the determination of a pulse in an amplitude modulated quantized analog signal having a signal amplitude complicating feature, comprising:

means for transmitting light through a specimen, means for monitoring the transmitted light to produce a data stream comprising values representative of the attenuation of light by the specimen over time, means for storing the series of values whereby each of the values is a discrete moment in time and the stored values are continually updated over time, wave form filter for evaluating the stored values over time whereby a series of filtered values are determined the filtered values including a plurality of extreme values representing the pulse, and means for determining a frequency of the extreme values in the series of filtered values.

2. A method for determining pulses in an amplitude modulated quantized analog signal having a signal complicating feature, comprising:

transmitting light through a specimen, monitoring the transmitted light to produce a data stream comprising a series of values representative of the attenuation of light by the specimen over time, storing the series of values whereby each of the stored values is a discrete moment in time, filtering the stored values whereby a series of filtered values are determined the filtered values including a plurality of extreme values representing the pulse, and evaluating the series of filtered values to determine a frequency of the extreme values.

3. An apparatus for the determination of a pulse in an amplitude modulated quantized analog signal having a signal amplitude complicating feature, comprising:

means for monitoring a data stream comprising a series of time spaced values, means for storing at least a portion of the series of time spaced values whereby the stored values are continually updated over time, wave form filter for evaluating the stored values over time whereby a series of wave form filter outputs are determined, the filter outputs including a plurality of extreme values representing the pulse, by solving the expression:

$$F_i = \sum_{j=i}^{L} (P_{i+j} - P_{i-j})$$

where $F_i$ is a wave form filter output for a given time $t_i$ having a data stream value $P_i$, $P_{i,j}$ is the data stream value at time $t_i - t_j$, and $p_{i+j}$ is the data stream value at time $t_i + t_j$, and data stream value at time $t_i + t_j$, and means for determining a frequency of the extreme values in the series of wave form filter outputs.

4. A wave form filter for the determination of pulses in an amplitude modulated quantized analog signal having a signal amplitude complicating feature comprising a means for generating the digital signal, the quantized analog signal comprising a series of time spaced values, a means for storing and continually updating at least three of the time spaced values, a filtering means to determine a filtered wave form by using at least two of the time spaced values the filtered wave form including a plurality of extreme values representing the pulses, and a means for determining the extreme values in the filtered wave form.

5. A method for determining pulses in an amplitude modulated quantized analog signal having a signal amplitude complicating feature comprising generating a modulated signal comprised of a series of time space data values, storing some of the data values which are continually updated over time, filtering the stored data values over time to determine a series of filtered values the filtered values including a plurality of extreme value in the signal representing the pulses, and evaluating the filtered values to determine the extreme values.

6. The apparatus of claim 1 wherein the amplitude complicating feature is a high noise level.

7. The apparatus of claim 1 wherein the amplitude complicating feature is a dicrotic notch.

8. The apparatus of claim 1 wherein the amplitude complicating feature is a baseline drift.

9. The method of claim 2 wherein the amplitude complicating feature is a high noise level.

10. The method of claim 2 wherein the amplitude complicating feature is a dicrotic notch.

11. The method of claim 2 wherein the amplitude complicating feature is a baseline drift.

12. The wave form filter of claim 4 wherein the amplitude complicating feature is a high noise level.

13. The wave form filter of claim 4 wherein the amplitude complicating feature is a dicrotic notch.

14. The wave form filter of claim 4 wherein the amplitude complicating feature is a baseline drift.

15. The method of claim 5 wherein the amplitude complicating feature is a high noise level.

16. The method of claim 5 wherein the amplitude complicating feature is a dicrotic notch.

17. The method of claim 5 wherein the amplitude complicating feature is a baseline drift.

* * * * *